(12) United States Patent
Jacobsen et al.

(10) Patent No.: US 6,553,880 B2
(45) Date of Patent: *Apr. 29, 2003

(54) MICROMACHINING SYSTEM

(75) Inventors: Stephen C. Jacobsen, Salt Lake City, UT (US); Clark Davis, Salt Lake City, UT (US)

(73) Assignee: Sarcos, LC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/908,445

(22) Filed: Jul. 17, 2001

(65) Prior Publication Data

US 2002/0078808 A1 Jun. 27, 2002

Related U.S. Application Data

(60) Continuation-in-part of application No. 09/470,606, filed on Dec. 22, 1999, which is a continuation-in-part of application No. 09/366,360, filed on Aug. 3, 1999, now Pat. No. 6,260,458, which is a division of application No. 08/714,555, filed on Sep. 16, 1996, now Pat. No. 6,014,919.

(51) Int. Cl.[7] .............................. B26D 5/02; B26D 5/20; B26D 7/02; B26D 7/06; B26D 7/26

(52) U.S. Cl. .............................. 83/75; 83/210; 83/211; 83/282; 83/361; 83/367; 83/368; 83/370; 83/421; 83/466.1; 83/486; 83/886; 83/422; 451/8; 451/9; 451/10; 451/381

(58) Field of Search .............................. 83/75, 62, 62.1, 83/63, 211, 367, 368, 370, 209, 210, 240, 248, 257, 282, 409, 418, 421, 465, 466.1, 422, 471.2, 471.3, 485, 486, 486.1, 556, 563, 733, 863, 864, 881, 886, 750; 269/245 R; 279/46.1; 451/8, 9, 10, 21, 381, 61

(56) References Cited

U.S. PATENT DOCUMENTS

| | | | | |
|---|---|---|---|---|
| 1,553,227 A | | 9/1925 | Feyk et al. ................ 83/409 |
| 1,866,888 A | | 7/1932 | Hawley ................. 83/471.3 |
| 3,664,066 A | * | 5/1972 | Clark, Jr. .................. 451/4 |
| 3,686,990 A | | 8/1972 | Margolien ............... 83/409 |
| 3,690,072 A | * | 9/1972 | Price ........................ 451/9 |
| 3,769,756 A | * | 11/1973 | Kipple et al. ......... 451/9 X |
| 4,000,672 A | | 1/1977 | Sitterer et al. ....... 83/209 X |
| 4,476,754 A | | 10/1984 | Ducret ................ 83/210 X |
| 4,545,390 A | | 10/1985 | Leary ................... 600/462 |
| 4,574,670 A | | 3/1986 | Johnson ................ 83/409 |
| 4,602,459 A | * | 7/1986 | Drifts et al. .............. 451/5 |

(List continued on next page.)

FOREIGN PATENT DOCUMENTS

| | | |
|---|---|---|
| DE | 1 507 057 | 9/1975 |
| EP | 0 123 456 B1 | 3/1984 |
| EP | 0 123 456 A2 | 3/1984 |
| EP | 06312313 | 8/1994 |
| GB | 2 257 269 A | 1/1993 |
| WO | PCT/US92/07619 | 3/1993 |

*Primary Examiner*—Charles Goodman
(74) *Attorney, Agent, or Firm*—Thorpe North & Western

(57) ABSTRACT

A micro-machining system configured for cutting an elongate object, including a clamp configured to enable repeatedly releasing and then holding the elongate object in a position suitable for cutting the elongate object transversely relative to its lengthwise axis, and a manipulating means, which can include a pinch roller feed configured to advance the elongate element and to rotate it about a lengthwise axis of the elongate object, thereby moving the elongate object so that it can be disposed in the position suitable for cutting, and a cutter configured for forming the at least one precision cut in the elongate object to a desired depth, under the control of a controller.

23 Claims, 9 Drawing Sheets

U.S. PATENT DOCUMENTS

| | | | | |
|---|---|---|---|---|
| 4,604,835 A | * | 8/1986 | Borin | 451/21 |
| 4,781,092 A | | 11/1988 | Gaiser | 83/282 X |
| 4,786,220 A | | 11/1988 | Fildes et al. | 409/134 |
| 4,884,579 A | | 12/1989 | Engelson | 600/585 |
| 4,922,777 A | | 5/1990 | Kawbata | 83/409 X |
| 4,954,022 A | | 9/1990 | Underwood et al. | 355/402 |
| 4,955,862 A | | 9/1990 | Sepetka | 604/164.13 |
| 4,989,608 A | | 2/1991 | Ratner | 600/420 |
| 4,994,069 A | | 2/1991 | Ritchart et al. | 606/191 |
| 5,009,137 A | | 4/1991 | Dannatt | 83/209 |
| 5,072,548 A | * | 12/1991 | Girard et al. | 451/21 |
| 5,095,925 A | | 3/1992 | Elledge et al. | 134/61 |
| 5,306,252 A | | 4/1994 | Yutori et al. | 600/585 |
| 5,308,435 A | | 5/1994 | Ruggles et al. | 83/209 X |
| 5,315,906 A | | 5/1994 | Ferenczi et al. | 83/282 X |
| 5,376,084 A | | 12/1994 | Bacich et al. | 604/515 |
| 5,437,288 A | | 8/1995 | Schwartz et al. | 600/585 |
| 5,438,993 A | | 8/1995 | Lynch et al. | 600/434 |
| 5,439,000 A | | 8/1995 | Gunderson et al. | 600/473 |
| 5,441,483 A | | 8/1995 | Avitall | 604/95.05 |
| 5,441,489 A | | 8/1995 | Utsumi et al. | 604/525 |
| 5,460,187 A | | 10/1995 | Daigle et al. | 600/585 |
| 5,477,856 A | | 12/1995 | Lundquist | 600/373 |
| 5,520,645 A | | 5/1996 | Imran et al. | 606/194 |
| 5,964,135 A | | 10/1999 | Aihara | 83/168 |
| 6,033,288 A | * | 3/2000 | Weisshaus et al. | 451/8 |

* cited by examiner

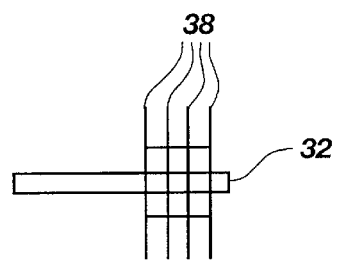
*Fig. 10*
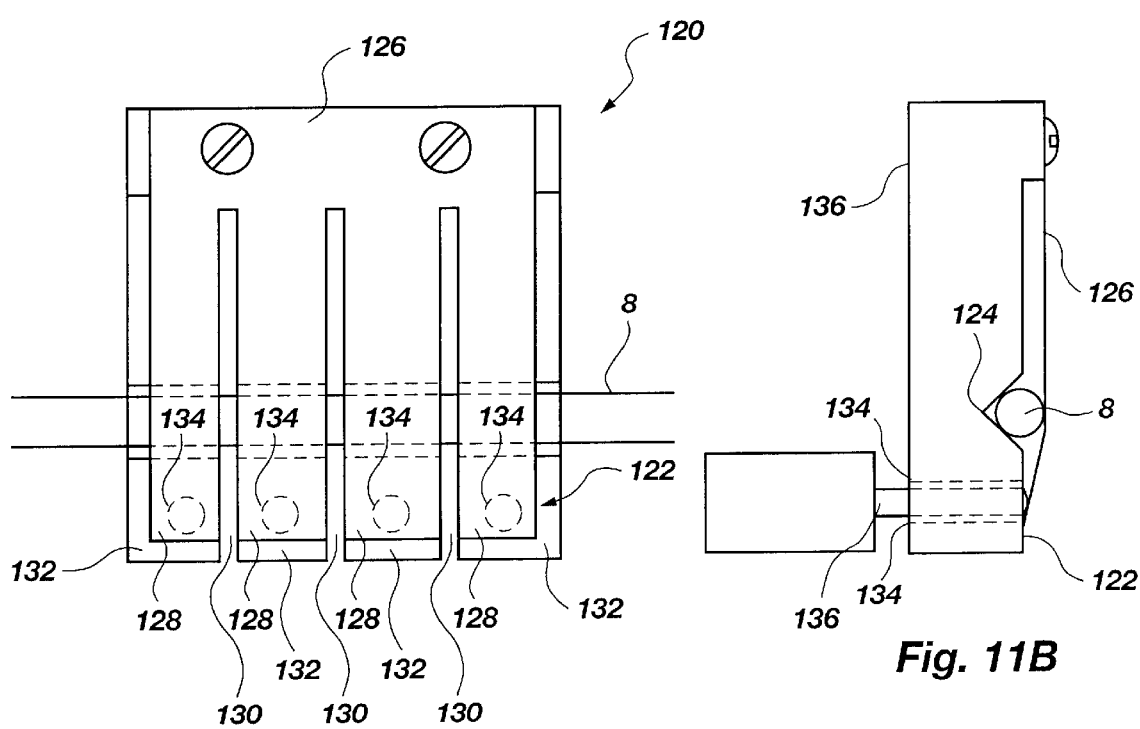
*Fig. 11A*
*Fig. 11B*

MICROMACHINING SYSTEM

This application is a continuation-in-part of co-pending U.S. Patent Application Ser. No. 09/366, 360, filed on Aug. 3, 1999, issuing Jul. 17, 2001 as U.S. Pat. No. 6,260,458, which is a divisional of U.S. patent application Ser. No. 08/714,555, filed Sep. 16 1996, now issued as U.S. Pat. No. 6,014,919, and is also a continuation-in-part of co-pending U.S. Patent Application Ser. No. 09/470,606, filed on Dec. 22, 1999.

BACKGROUND

1. Field of the Invention

The invention relates generally to methods and apparatus for machining on a relatively small scale. More particularly, the invention relates to systems for making precision cuts in small elongate objects, such as solid and tubular elements usable in invasive medical devices such as catheters and guidewires.

2. Description of Related Art

Making cuts in small solid and tubular elongate elements, for example such as wires and tubular elements used in catheters and guide wires, requires precision in order to ensure that the desired functional characteristic are achieved, and that such characteristics are achieved with reliability. However, it is also important to control costs of production.

The state of the art is typified by such devices as grinding devices for changing outer diameter of an elongate element, and by electron discharge machining (EDM) devices and laser devices for making cuts in the elongate member, and lithographic-like processes for selective removal of material. Such devices can involve relatively high cost, and in the case of lithographic processes can involve a number of separate steps. In the case of laser and EDM, machining processes, due to the nature of such devices, a finished product of less than desired quality can initially result, since heating and/or ablation of the material is involved, giving rough cut qualities and/or locally altering the material by heating, melting, thickening or thinning, so that it has less desirable properties. Also, manipulation and control systems can be a factor, as imprecise control and manipulation mechanisms for properly positioning the cutting means of the device to make the cut, as well as the elongate object to be cut, can give rise to less than desired quality of a finished product.

SUMMARY

It has been recognized that using a micro-saw blade, such as is typically used in the microchip fabrication arts, can give superior results in cutting material in a micromachining process. It has further been recognized that what is needed is a method and apparatus for making cuts in catheters and guide wires which allows precise control of characteristics of the cuts. This also entails precision holding, advancement and rotation of a generally elongate, and typically cylindrical, object while at least one microsized saw blade is advanced to make a cut to a precise depth and retracted afterward.

The invention accordingly provides a micro-machining system configured for cutting an elongate object of small transverse dimension having a lengthwise axis, comprising: a) a controller programable to enable control of cuts in the elongate object with respect to each other in terms of position along and around the lengthwise axis and to a depth desired; b) a clamp configured to enable repeatedly releasing and then holding the elongate object in a fixed position for cutting the elongate object transversely relative to the lengthwise axis; c) a pinch roller feed configured to advance the elongate element and to rotate it about a lengthwise axis of the elongate object, thereby moving the elongate object so that it can be disposed in a position for cutting; a contact reference position sensor; and, d) a cutter configured for forming the at least one precision cut in the elongate object to a desired depth into the elongate object from the sensed first contact by the cutter with the elongate object.

In another inventive aspect the system for micromachining an elongate element having a lengthwise axis can comprise: a) a controller configured to control operation of the system, programable to produce micro-machined elongate elements of desired configurations; b) a clamp configured to engage and release the elongate element under control of the controller; c) manipulating means configured to move the elongate element along its lengthwise axis and to rotate the elongate element about its lengthwise axis under the control of the controller, further comprising an actuator controlled by the controller configured to rotate the elongate element, and an actuator controlled by the controller configured to move the element along its lengthwise axis; d) an actuator-moved saw blade configured to form cuts of small dimensions in the elongate element and to be movable toward and away from the elongate element by an actuator under control of the controller, further comprising an actuator configured to move the saw blade toward and away from the element under control of the controller, and, e) a contact reference point identification system configured to provide a signal interperatable by the controller indicating that the saw blade has approached the element and just made contact therewith without appreciable depth of cut, the system being configured to control depth of cut from a contact reference point into the elongate element by the saw blade; whereby the element can be clamped to hold it in a fixed position, and a first cut of precisely controlled depth can be made, and the element can be released and at least one of rotated and moved along and about its lengthwise axis and a second precise cut made of a desired depth in a desired position in relationship to the first cut.

In a more detailed aspect the cutter can be a rotating cutting blade forming a kerf of a small width (as used in chip manufacturing for example) that is less than 0.003 inches wide. In another more detailed aspect, the contact reference position sensor can comprise an electric circuit completed by contact between the cutter and the object. The contact reference position sensor can comprise an optical sensor which senses contact between the cutter and the object. Where the cutter is a saw blade the contact reference point identification system can comprise an electrical circuit completed by contact of the saw and the elongate element. This can be a DC circuit . This circuit can be an AC circuit. Proximity of the cutter to the elongate object can be sensed by induced current from an element of the AC circuit before contact is made.

In another more detailed aspect, movement of portions of the system with respect to each other can be facilitated by stepper motors controlled by the controller. A stepper motor under control of the controller can be configured to actuate at least one of the manipulating means and the actuator-moved saw blade. A stepper motor under control of the controller can be operatively coupled to the manipulating means to advance the elongate element, and a stepper motor under control of the controller can be operatively coupled to the manipulating means to rotate the elongate element. An actuator facilitating movement of the saw blade toward and away from the element can comprise a caliper and a stepper motor operatively connected to the caliper, configured to position the saw with respect to the element with precision, whereby a depth of cut with respect to the contact reference point can be precisely controlled.

In a further more detailed aspect, a position sensor can be provided, configured to sense movement of the blade toward and away from the element, wherein feedback control of blade position is facilitated. The sensor can be one of a LVDT and a LVDC.

In a further more detailed aspect, the system can be configured to sense at least one of a) an amount of blade wear on a cutter comprising a cutting blade; b) an asymmetry of the elongate element about its lengthwise axis at a given point along its length. The system can be configured to quantify one of an asymmetry and an out-of-round condition of the elongate element.

In another inventive aspect the system for forming cuts in a small-diameter elongate element having a lengthwise axis can comprise:

a) a controller configured to control operation of the system, programable to produce micro-machined elongate elements of desired configuration in diameter sizes usable as catheters and guidewires for invasive medical procedures in a human body;

b) a clamp configured to engage and release the elongate element under control of the controller;

c) manipulating means including a pinch roller assembly configured to grasp the elongate element, and move the elongate element along its lengthwise axis and to rotate the elongate element about its lengthwise axis under the control of the controller, further comprising an actuator comprising a stepper motor controlled by the controller configured to rotate the elongate element, and an actuator comprising a stepper motor controlled by the controller configured to move the element along its lengthwise axis;

d) an actuator-moved saw blade configured to form cuts of small dimensions in the elongate element and to be movable toward and away from the elongate element by an actuator comprising a stepper motor turning a caliper under control of the controller, wherein the actuator is configured to move the saw blade toward and away from the element under control of the controller; and, e) a contact reference point identification system comprising an electrical circuit configured to provide a signal interperatable by the controller indicating that the saw blade has approached the element and just made contact therewith without appreciable depth of cut, the system being configured to control depth of cut from a contact reference point into the elongate element by the saw blade, whereby the element can be clamped to hold it in a fixed position, end a first cut made, then it can be released and moved by being at least one of rotated and moved along and about its lengthwise axis, and a second precise cut made to a desired depth at a desired position in relationship to the first cut.

BRIEF DESCRIPTION OF THE DRAWINGS

FIG. 10 is a side elevational view of a saw blade arrangement in another embodiment.

FIG. 11A is a side view of a clamp which can be used with the saw blade embodiment of FIG. 10.

FIG. 11B is a front view of the clamp arrangement shown in FIG. 11A.

DETAILED DESCRIPTION OF THE PREFERRED EMBODIMENT(S)

Figure 1A:
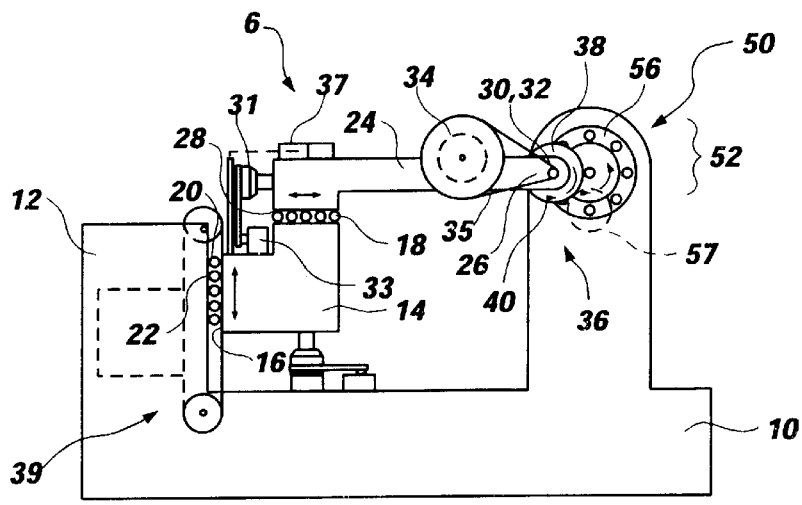
FIG. 1A is a front elevational view of a one embodiment made in accordance with the principles of the present invention.
Figure 1B:
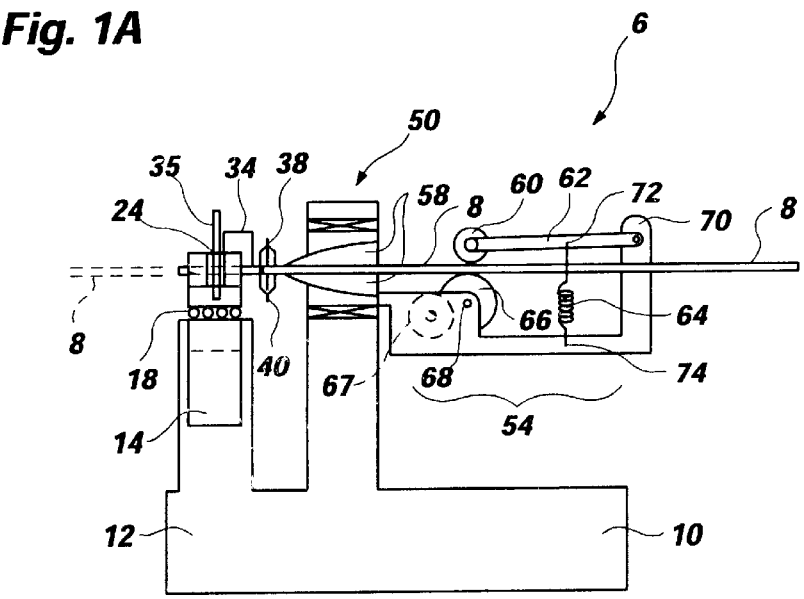
FIG. 1B is a side elevational view of the invention shown in FIG. 1A.

With reference to FIGS. 1A and 1B of the drawing figures, which are given by way of example, and not by way of limitation, in one embodiment of the invention, a system 6 for forming precision cuts in a catheter, a guide wire, or other cylindrical objects is illustrated. For purposes of illustrating features of the invention, an example of a length of tubing 8 which when micromachined can be used in a guidewire or catheter will be referred to as the object being cut. However it should be understood that the system can be used to micro-machine other small generally elongate objects. Such objects can have a variety of cross-sectional shapes, such as box tube, rectalinear bar, oval solid and tubular shapes, etc., although cylindrical solid and tubular objects will probably be more commonly machined, and the examples shown will illustrate and describe a cylindrical object—a tube as mentioned. Reference to the tube is only for the convenience of writing in terms of a specific cylindrical object, and should not be considered a material limitation of the invention. However, referring to a tube used in a catheter or guidewire keeps present in mind the objective of having a very precise cutting device, where it is recognized that precision is usually very important in most medical applications.

The system 6 shown in FIGS. 1A and 1B includes a base member 10 configured for carrying and supporting the various elements of the system. Coupled in sliding engagement with a vertical base member 12 is a vertically movable member 14 which has a first vertical coupling face 16 and a first horizontal coupling face 18. The vertical coupling face 16 is slidingly engaged with a base member vertical coupling face 20.

The mechanism 22 for enabling the sliding engagement between the vertical coupling face 16 and the base member vertical coupling face 20 can be any appropriate apparatus. The important consideration is that the vertically movable member 14 not be permitted to move horizontally, or the precision of the system will be compromised. Therefore, the tolerances of the mechanism 22 must necessarily be small. A good example of an appropriate mechanism 22 is well known to those skilled in the art as a crossed roller bearing slide.

Figure 2:
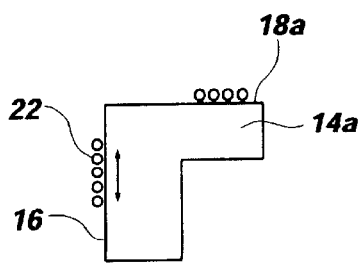
FIG. 2 is another embodiment of a vertically moving member shown FIGS 1A and 1B.
Figure 3:
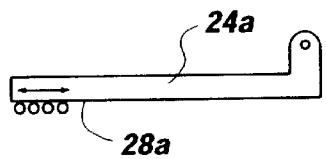
FIG. 3 is another embodiment of a horizontally moving member shown in FIGS. 1A and 1B.

The shape of the vertically movable member 14 is shown here as a small backwards "L". An alternative shape for a vertically movable member 14a is shown in FIG. 2. The member 14a is flipped over as compared to the embodiment of FIG. 1A. The important feature of the member 14a for this discussion is that it provides two faces 16 and 18a which can be slidably engaged to move vertically and provide a second face on which another member can slidably engage to move horizontally. Similarly, another embodiment of a horizontally moveable member 24a is illustrated in FIG. 3. Here, a horizontal coupling face 28a is shown substantially coplanar with the horizontally moveable member 24a.

The system in FIGS. 1A and 1B also includes a horizontally movable member 24 which has a spindle end 26 and a second horizontal coupling face 28. This horizontally movable member 24 is slidably engaged at its second horizontal coupling face 28 to the vertically movable member 14 at its first horizontal coupling face 18. This again can be by one of many suitable means, such as by a crossed roller bearing slide. Smooth action and close tolerances are important, and may directly affect the quality of the micromachined element 8 produced by the system 6. It should be observed that the vertically movable member 14 and the horizontally movable member 24 are capable of moving independently of each other. Therefore the horizontally moveable member in the illustrated embodiment actually can move vertically, horizontally and diagonally, and not just horizontally. In another embodiment the horizontally movable member attaches directly to the base 10 or to other structure carried by the base. In this embodiment the blade moves directly toward and away from the elongate element 8. The attachment is by a crossed roller bearing slide or other suitable means allowing relative translating movement of the horizontally movable member. Also, it should be notes that while in most cases the horizontally movable member will move substantially horizontally, that this is not necessarily the case for all embodiments. For example, in the embodiment where the horizontally moveable member is slidably attached to the base, in one embodiment the member can translate toward and away from the elongate member 8 to be cut along an inclined plane. Accordingly a more general appropriate appellation is "movable member."

The movable member 24 is actuated in one embodiment by a finely treaded screw drive such as a relatively precise rotating micrometer caliper head 31 head turned by a relatively precisely controllable stepper motor 33. If desired, feedback position information can be supplied by a position sensor 37 which can comprise a linearly variable differential transformer (LVDT) or another appropriately sensitive position sensor.

The vertically movable member 14 can be likewise actuated, and in one embodiment a counterbalance arrangement 39 is provided. Alternatively, other types of actuators can be used, such as a hydraulic actuator, a geared actuator rotatably coupled to the counterbalance arrangement, a worm gear arrangement, to name a few examples.

The spindle end 26 of the horizontally movable member 24 provides a horizontally disposed cylindrical journal 30 in which a spindle 32 is disposed, or it carries bearings, sleeves or other structure for this purpose. The journal 30 is generally circular to serve as a receptor for the round spindle 32. Air or other fluid can be used in bearings or the journal, and ball bearings, needle bearings, or other conventional bearings usable for sustained high-rpm use can be employed. The spindle shaft has disposed on a working end 36, thereof at least one circular saw blade 38. The circular saw blade 38 is disposed vertically on the spindle shaft, but may also be angled by tipping the spindle in other embodiments. The saw blade is conventional in other application, for example it can be of the type used in semiconductors manufacturing to separate individual chips from a wafer after fabrication. Such blades are widely commercially available. They typically comprise a relatively thin outer ring 40 of abrasive material, such as a diamond grit in an adhesive matrix. The outer ring is typically less than three thousandths of an inch thick, and usually about two thousandths of an inch thick, and accordingly produces a kerf of approximately this same width. The blade is reinforced, and is typically considerably thicker inside of the said outer ring comprising the cutting material.

The spindle 32 is coupled to a drive motor 34 by gears, belts, direct drive, or any other appropriate means which will cause the spindle 32 to rapidly rotate. The drive motor can be disposed in an appropriate location relative to the spindle shaft. In one embodiment, the spindle shaft 32 and attached blade 38 are driven by a brushless DC motor through a toothed timing belt 35.

One means for holding and otherwise manipulating a guidewire, catheter, or other elongate object 8 to be cut is a clamping member 50. The clamping member 50 illustrated in FIGS. 1A and 1B includes two assemblies: a clamp 52; and a clamp feeding (supplying) means 54 comprising an assembly which feeds the guidewire or catheter element or other elongate object 8 toward and then through the clamp 52. The clamping member 50 is also coupled to the base member 10 and disposed to hold the clamp 52 in a position for feeding of the guidewire or catheter element or other elongate object 8 to the circular saw blade 38 and holding it immovable in close proximity to where the blade 38 will form a kerf in the elongate object as it is advanced toward and into the material comprising the elongate object.

In one embodiment, the clamp 52 is of the type known as a collet clamp. An example of a collet clamp is a slotted cylindrical clamp inserted tightly into the tapered interior of a sleeve or chuck on a lathe to hold a cylindrical piece of work. In FIG. 1A, the cylindrical shape of the clamp 52 is visible. It is slotted in that two or more clamping arms 58 are separate from each other so that they can pull away from the guidewire or catheter element or other elongate object 8 when disengaging, and then securely come together around the guidewire or catheter element or other elongate object 8 when engaging.

In a preferred embodiment, a desirable feature of the collet clamp 52 is that it is rotably mounted within the clamping members 50 with respect to the base 10. The collet clamp 52 can then rotate so as to dispose a different portion of the surface of the guide wire or catheter element or other elongate object 8 to the saw blade 38. The mechanism for rotating the clamp 52 is shown generally at 56, and is comprised of the clamp 52 which is held in a frame which can rotate with respect to the saw blade 38 by means of a stepper, motor 57. Position feed back can be provided by a rotating variable transformer (not shown), optical encoder or other similarly sensitive position sensing device adapted to indicate rotational position of the clamp 52 with respect to the blade 38.

The clamp feeding (supplying) means 54, best seen in FIG. 1B, is a pinch roller assembly 60, 62 working in conjunction with a feed roller 66. The entire clamp supplying means is rotatable with the clamp 52 about a lengthwise axis of the elongate object 8. In one embodiment it is fixed to the collet clamp portion rotatable within the frame carried by the base 10. As best appreciated with reference to FIG. 1B, the pinch roller assembly 60, 62 feeds the guidewire or catheter element or other elongate object 8 toward the clamp 52 by friction created between two opposing roller members 60, 66. The upper member is the pinch roller 60. The lower member is the feed roller 66. One or both of the a rollers is comprises an elastomeric material having a relatively high coefficient of friction. The feed roller 66 has an axle 68 mounted in the clamp feeding means 54 so that the feed roller 66 can roll, actuated in a controlled manner by a stepper motor 67. The pinch roller 60 is disposed at the end of a lever arm 62 which pivots at a pivoting end 70. Located distally from the pinch roller assembly along the length of the lever arm is a hole 72. One end of a spring 64 is inserted therethrough, and the other end of the spring 64 is coupled at another hole 74 to the clamp feeding means 54. The spring 64 provides the tension necessary to generate sufficient friction for the feed roller 66 to hold and to push the elongate object 8 toward the clamp 52, but not so much as to deform the elongate object beyond the elastic range of the material from which it is formed.

In operation, the illustrated embodiment of the guidewire or catheter element or other elongate object cutting assembly 6 functions in accordance with the description that follows. First, the uncut element of a catheter or guidewire, or other elongate object 8 is placed between the pinch roller 60 and the feed roller 66. This can be done by raising the lever arm 62 by stretching the spring 64. Subsequently releasing the lever arm 62 causes the pinch roller 60 to push down against the feed roller 66, with the guidewire or catheter element or other elongate object 8 disposed therebetween. A drive mechanism including the stepper motor 67 is coupled to the feed roller 66 to cause it to roll and thereby push the elongate object toward the clamp 52. It will be appreciated that the feeding means 54 can be reversed to pull the elongate member in a direction back out of the clamp 52, but in usual operation the elongate object will feed in one direction as it is not desirable in most circumstances to draw a portion of the elongate object already micromachined by operation of the system 6 back into the clamp. The clamp 52 will be in a disengaged position (hole through clamp is larger than diameter of the guidewire or catheter element or other elongate object 8) so that the guidewire or catheter element or other elongate object 8 can be fed easily therethrough. After passing through the clamp 52, the catheter or guidewire element or other elongate object 8 is fed sufficiently far past the circular saw blade 38 so that it is in a proper position to have an incision (kerf) made in or through a surface of the elongate object facing the blade.

When the catheter element, guidewire element, or other elongate object 8 is positioned correctly to make a cut therein, the clamp 52 is engaged to hold the object securely at a location adjacent the turf to be made, and the saw blade 38 is advanced to make cutting contact. Before cutting, the saw blade 38 will be positioned in a retracted position, away from the elongate object. The retracted position can be either or both vertically above or below and horizontally pulled away from the guidewire or catheter element or other elongate object 8. If there is only a horizontally movable member 24, then the motion is substantially horizontally toward and away from the elongate object. Because the diameter of the saw blade 38 is so much greater than the diameter of the typical elongate object being cut, it is assumed that the blade makes essentially a vertical curf. If the blade is inclined, or is made to contact the elongate object slightly off-center above or below, then it is assumed that the cut is in the plane of a cord line of the blade circumference, and the depth of the cut corresponds to the location of a cord line of the blade circumference having a length corresponding with the length of a cord of the circumference of the elongate object corresponding with the ends of the curf if the elongate object is cylindrical, or corresponding with a simple straight a line connecting the ends of the curf for other crossectional shapes. As will be appreciated, if the horizontally movable member 24 is configured to cut the elongate object by horizontal movement above or below the elongate object then the cuts will be of uniform depth and straight through the object, ignoring blade wear. To compensate for blade wear in the later embodiment the position of the horizontal member 24 can be adjustable in one embodiment. An example of how this may be done is providing the vertically movable member 14 and other structure as described above, but other methodologies can be employed. Accordingly, one method of operation is to set the depth of cut by vertical movement and then repeatedly moving the blade back and forth horizontally. The positions of the cuts are determined by rotation and translation of the elongate object by the manipulating means 54 and/or the manipulating means with the rotatable clamp 52.

In another embodiment the cut can be made by providing both vertical and horizontal movement, and actuating the vertically and horizontally movable members so the first movement of the saw blade 38 is a horizontal advancement toward the guidewire or catheter element or other elongate object 8 to a desired depth of cut. This is accomplished by moving the horizontally movable member 24 relative to the vertically movable member 14 to which it is attached. The horizontally movable member 24 is moved toward the object until it has reached the desired depth of the incision to be made in the guidewire or catheter element or other elongate object 8. The next step comprises moving the vertically movable member 14 upwards or downwards (depending on whether it is brought above or below the elongate object in the previous step) relative to the object (as well as the base 10 to which it is movably coupled) to thereby make the cut. The saw blade 38 is then retracted by moving the vertically movable member 14 away from the guidewire or catheter element or other elongate object 8. In one embodiment the horizontal member is moved only when the next cut is at a different depth or when all cutting is complete, or an adjustment for blade wear is desired.

If, as usually will be the case, multiple cuts are to be made, the collet clamp 52 is released and the elongate object is moved between cuts. The guidewire or catheter element or other elongate object 8 is typically fed through the clamp 52 by rotation of the feed roller 66 to a desired lengthwise position of the next cut along the catheter length. The elongate object is then rotated so that the rotational position of the cut will be as desired. The collet clamp 52 can be re-engaged at any time after the longitudinal advancement of the elongate object but before cutting. If so programmed, the system 6 can rotate the elongate object only when the collet clamp 52 is closed, thereby further supporting the elongate object as it is rotated to expose a different position of the elongate object 8 to the saw blade 38.

As will be appreciated, the horizontal or vertical position can be held relatively constant, and the other of the two be the direction of blade 38 travel in machining operations. In this embodiment the saw blade 38 is moved horizontally or vertically if the depth of cut is to change, and then vertically or horizontally, respectively, to make the cut. In all embodiments the steps outlined above are repeated as often as necessary until all the desired incisions have been made, which may correspond to the timer the guidewire or catheter element or other elongate object 8 is no longer capable of being grasped by the feed roller 66 and opposing pinch roller 60.

Figure 13:
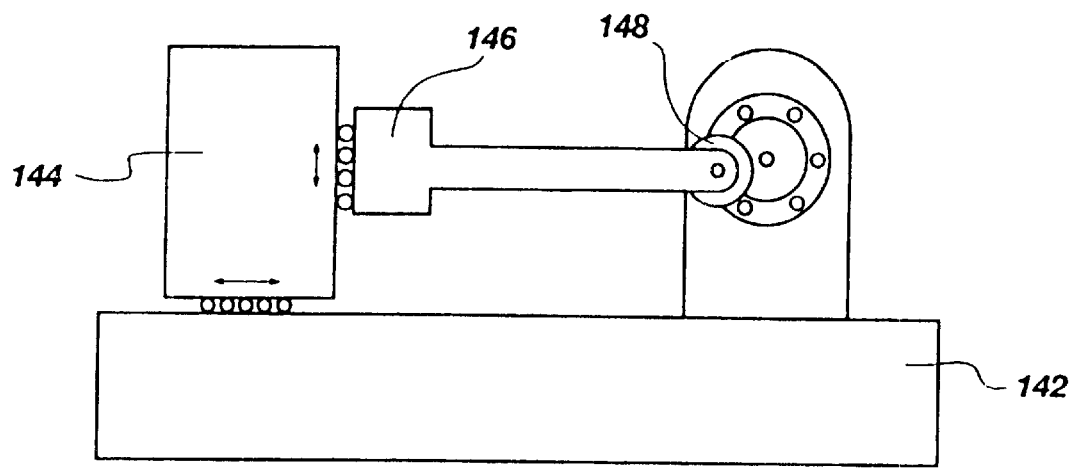
FIG. 13 is a front view illustrating another embodiment.

With reference to FIG. 13, it should be noted that while an embodiment has been described above having a horizontally movable member with the spindle for the saw blade coupled thereto, the placement of the vertically and horizontally movable members can be switched, as shown in FIG. 13. In this arrangement, the horizontally movable member 144 is coupled to the base member 142 and the vertically movable member 146, and the vertically movable member 146 has a spindle 148 rotatably coupled thereto. Otherwise the device functions as described above.

Figure 14:
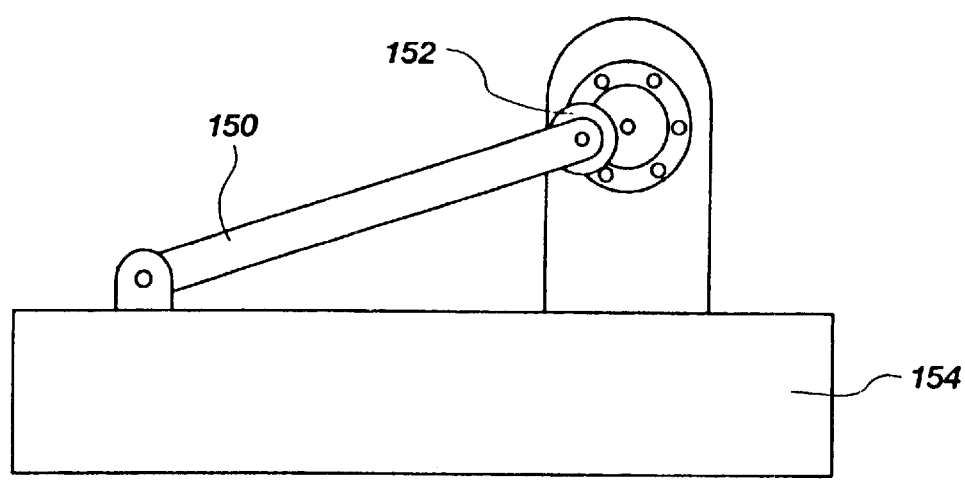
FIG. 14 is a front view illustrating another embodiment.

With reference to FIG. 14, in another embodiment of the invention, a lever arm 150 is pivotally connected to the base member 154, and forms cuts in the elongate object 8 to a depth determined by the length of the lever arm from the pivot to the blade 38 at a spindle end 152. An actuator (not shown) such as the micrometer caliper head described above, can be placed in between the arm and the base 154. Alternatively, in this embodiment movement of the arm can be accomplished by a geared drive (not shown) incorporating a stepper motor and reduction gearing to provide controlled rotational movement of the pivot arm around its pivot axis. In one embodiment the length of the pivot arm can be made variable, for example by incorporating a telescoping arrangement for the pivot arm and a micrometer caliper head (not shown) to extend or retract the arm to change its length. The actuation for changing the length of the arm can further incorporate a stepper motor (not shown) to actuate the caliper head as discussed above in connection with other embodiments.

Figure 15:
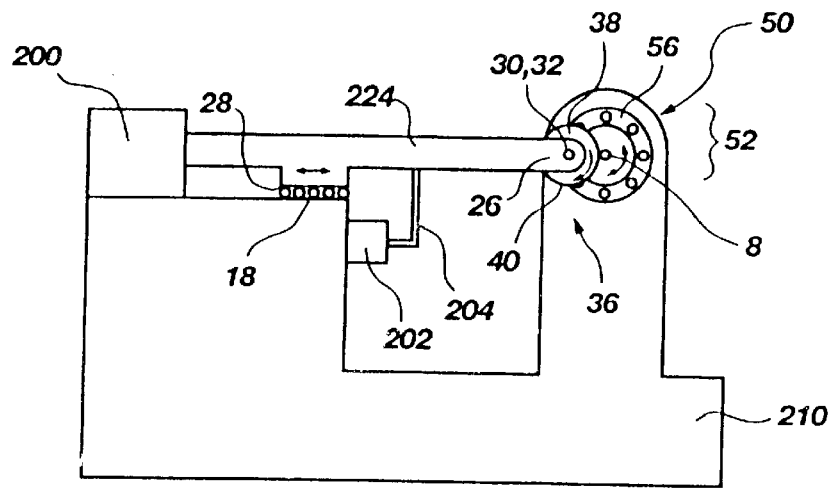
FIG. 15 is a front elevation view illustrating another embodiment.

With reference to FIG. 15, in ore embodiment mentioned above, a vertically moveable member is omitted, and a horizontally movable member 224 carrying the blade 38 moves toward and away from the elongate object 8 to provide the cutting action. This embodiment is similar in most respects to that illustrated in FIGS. 1A and 1B and includes most of same elements. The horizontally movable member 224 is slidingly coupled to base member 210 at horizontal coupling face 18, for example by a crossed roller bearing slide. In this embodiment the horizontally movable member is vertically positioned so that the center of blade 38 is in substantial alignment with the center of the guidewire or catheter element or other elongated element B.

Horizontally movable member 224 is also connected to the base 210 through, and is actuated for horizontal movement with respect to the base by, a linear motion actuator 200 which is affixed to base 210 at one end and the horizontally movable member 224 at the other. The linear motion actuator can comprise one of the many devices suitable for causing very accurate, controllable forward and backward horizontal motion of member 224. Such an actuator can comprise for example an electric motor with a reduction gear set, including a gear set having a worm gear, rack and pinion gears, or scissors with a threaded jackscrew, or some other arrangement suitable to convert rotational movement to translational movement; or can comprise a finely controllable hydraulic pump and piston system, etc. In one embodiment the linear motion actuator 200 comprises an electric stepper motor, coupled by a belt or gears to a micrometer caliper head or like device having fine threads for giving controlled linear movement in response to a rotational input. The micrometer caliper head is connected at one end to the base 210 and at the other to the horizontally movable member 224. This configuration advantageously causes horizontal motion of the horizontally movable member in a predictable manner in very small increments by stepping the stepper motor.

Also disposed between the base 210 and the horizontally movable member 224 is a position sensor 202, which is connected via linkage 204 to the horizontally movable member. The sensor provides independent detection and measuring of the forward or backward movement and/or position of horizontally movable member 224 with respect to the base, and is connected to the controller 80 for enabling position feedback control of the position of the blade 38 and control otherwise as described in more detail below. The sensor 202 can be an optical linear encoder, a LVDT, a linearly variable differential capacitor (LVDC), or any other suitably accurate means of measuring the physical position of member 224 with respect to the base, and by extension to the elongate member 8 to be machined. Alternatively, a rotary optical encoder or rotary differential capacitor can be used with the rotating portion of the micrometer caliper head to give such position feedback, assuming accurate functionality of the caliper head. Optical encoders, LVDT's, LVDC's, and other suitable position sensor devices are commercially available, and well known to persons skilled in the art.

The sensor 202 is optional, however. As an alternative, the extension and retraction of member 224 may simply be monitored through monitoring the stepping of the stepper motor, as each step corresponds with a known amount of rotation, and by means of the micrometer caliper head a known amount of linear motion. By counting stepper motor steps from a known reference position the position of the blade with respect to the elongate object can be determined.

The monitoring of position in any case will include software programmed into the controller that correlates a signal from the sensor or a counted number of steps of the stepper moron to a position for the horizontal member 224, and thus the blade 38 to another embodiment, by way of example to illustrate this principle, a rotary optical encoder may be interconnected to a gear reduction system such as a micrometer caliper head incorporated in the actuator 200, and the system will gauge the amount of linear extension of member 224 by the software monitoring the net angular rotation from a reference point of the optical encoder at any given time. Rotation of the micrometer caliper head can be by a gear reduction system in this embodiment and need not be by a stepper motor necessarily; as an electric motor with appropriate reduction gearing to the caliper head may be controlled by means of the software programmed into the controller which receives feedback from the optical encoder enabling calculation of linear position.

Nevertheless, in one embodiment at least one independent position sensing capability provided and is used to advantage in more precisely machining the elongate object 8 such as a catheter element or guidewire element, by accurately locating the point of first contact between the blade 38 and the object, and then monitoring the depth of cutting into the elongate object.

In general an important component of the system 6 is a position sensing means. For example, how the system determines how far to advance the elongate object between cuts, or how far and in what direction to rum it, as well as how deep to cut as just mentioned, implies there is some methodology for precisely sensing, and/or controlling, movement, so that machining operation will be repeatable and accurate. In other words, precision cutting also requires precision positioning of the catheter. Precise positioning requires the accuracy in controlling the movement of the elongate object and the blade with respect to each other. Sensors can be provided which can detect where the elongate object 8 is in relation to the saw blade 38 and the clamp and then provide information to a controller 80 which coordinates movement of all components by sending the necessary signals to correctly position all of the system 6 components for each cut made in the machining process.

Figure 4:
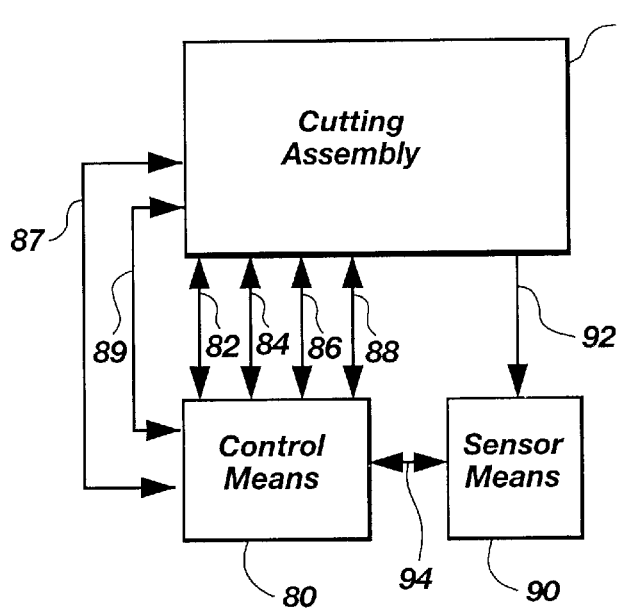
FIG. 4 is a schematic illustration of the system in a block diagram showing the interrelationship of the cutting assembly control means and sensor means.

This concept is shown generally in the block diagram of FIG. 4. The elongate object cutting system 6 in one embodiment is shown as having inputs from a controller 80 configured for positioning the vertically movable member 14 and shown as arrow 82, the input shown as arrow 84 for positioning the horizontally movable means 24, the arrow 86 which designates an input for controlling rotation of the manipulating means 54 and/or the clamp 52, and an arrow 88 which designates an input for controlling the feed roller 66. Two control inputs for the clamp and the spindle motor are also shown as arrows 87 and 89, respectively. The block diagram in FIG. 4 also shows a sensor means 90 for receiving position information from the system 6 as indicated by arrow 92. This information is transmitted to the control means 80 as indicated by arrow 94 so that it can be processed and the correct control signals 82, 84, 86, and 88 can be transmitted to the system 6. The sensor means can be one or many sensors depending on how much position feedback information is desired to implement the particular control algorithm chosen.

Figure 5:
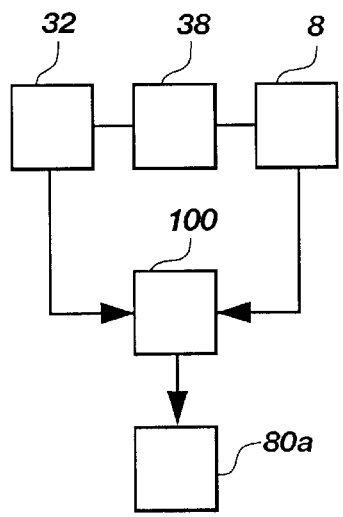
FIG. 5 is a block diagram which illustrates schematically a contact sensor system one embodiment.

For example, there are several alternative methods for determining the position of the elongate object 8 relative to the saw blade 38. In one embodiment the sensor means 90 can include an electrical conduction sensing circuit 100 shown in block diagram form in FIG. 5. It is sometimes the case that the materials used in elongate objects 8 are electrically conductive. Furthermore, the saw blade 38 can also be electrically conductive. Consequently, bringing the saw blade 38 into contact with the conductive elongate object 8 can result in the completion of an electrical circuit. By moving the saw blade 38 sufficiently slowly so as not to abruptly make contact with the elongate object 8, the moment of contact can be used as a reference point so that the saw blade 38 can be moved the proper horizontal distance to make the desired depth of cut into the elongate object from the blade's first contact with its surface.

Figure 6:
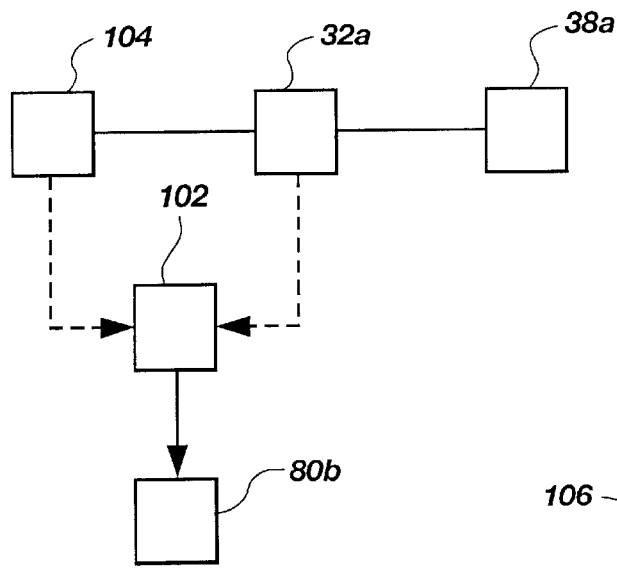
FIG. 6 illustrates another embodiment of a contact protection system.

FIG. 6 illustrates an alternative method of relative position sensing. In this embodiment, a mechanical drag detection means is coupled to a saw blade 38a. The drag detection means 102 ran be coupled to either the driving means 104 of the saw blade 38a, or a spindle 32a of the saw blade 38a. In other words, the drag detection means 102 is any suitable device for detecting when a dragging force is encountered by the saw blade 38a. For example, one device for this purpose is a torque transducer which measures the torque loading of the shaft which turns the blade 38a. In one embodiment the power drawn by the motor 34 is monitored and an increase in power required indicates an increase in torque loading. Particularly when coupled with proximity of the blade to the elongate object known or inferred by the control system and subsequent increase in torque as the blade encounters more material in extending the kerf into the elongate element, and calibration of the system with respect to power demand increase with depth of cut at the first part of cutting operations on an object formed of a known material and geometry, very precise indication of the time and/or blade location at first contact can be had. Subsequent fine control of further movement of the blade toward the element enables precise depth control.

Figure 7:
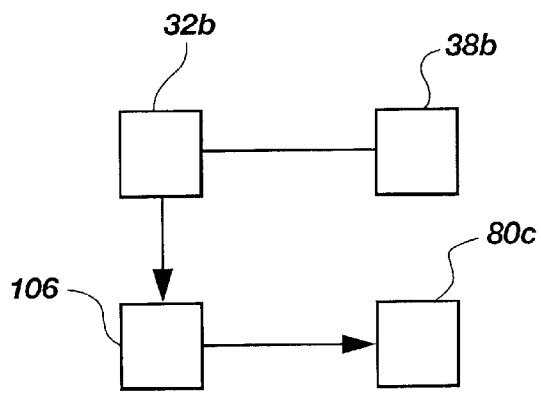
FIG. 7 is a block diagram schematically illustrating another embodiment of a sensing system.

FIG. 7 illustrates in another embodiment a method of position sensing using a rotation detector means 106. One method is to detect a slight decrease in rotational speed without corresponding drop in power to the motor, indicating cutting contact. This can be combined with sensing power drawn in the previously discussed embodiment to provide improved indication of first contact of the blade with the elongate object. In another embodiment a rotation sensor which detects even slight partial revolutions of the saw blade 38b can be used. As the spindle is oscillated vertically and slowly advanced horizontally, this slight rotation is detected. With the blade 38b not spinning, rotation of the blade 38b will occur when slight contact is made between the blade with the elongate object as the blade is being moved horizontally or vertically in a back-and-forth manner. Therefore oscillating the blade in one direction while advancing it in an orthogonal direction toward the elongate object will give detection of contact.

In another embodiment first contact can be sensed by a change in vibration, particularly audio vibrations, in the vicinity of the point of contact of the blade 38 and elongate object 8. For example the pitch of the sound vibrations from the rotating blade will change upon contact and this change can be sensed by an audio transducer and appropriate circuitry.

Figure 8:
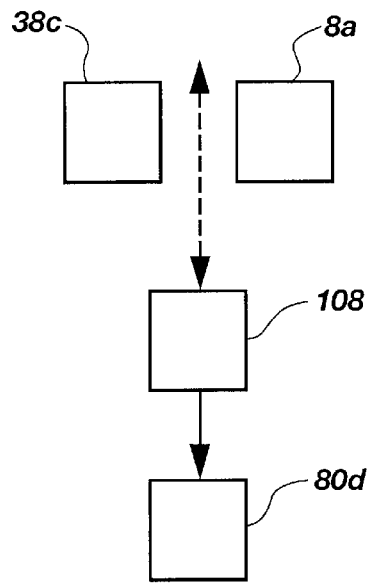
FIG. 8 is a block diagram which schematically illustrates a sensing system in an embodiment.

Another, embodiment of a sensor 90 configured for detecting the position of a saw blade 38c relative to an elongate object 8a to use an optical detector 108, as illustrated in block diagram form in FIG. 8. The optical detector means 108 is disposed such that it can detect contact between the saw blade 38c and the elongate object 8a. There are various optical devices which can be used to implement this detector 108, such as a light beam and defector, the light beam being detectably altered by contact. Alternatively an image capture device and appropriate software to analyze image data continually and detect a contact can be used. For example the first contact of shadow of the blade and of the elongate object in light beam projected across them and onto a charge coupled or charge injected imaging chip array can be detected to indicate first contact.

With the forgoing numerous varied examples it will be appreciated that many means of contact detection are possible. Further detail regarding the conductivity method mentioned above will be given below.

One aspect of the invention which is related to the various sensing means 90 described above is that not only is it important to know the position of the blade, but it is also important to know the degree of wear of the blade. All of the sensor embodiments above are inherently able to compensate for the wear which the blade 38 will experience. In other words, none of the methods for determining the exact position of the blade 38 rely on an assumption that the size of the blade 38 is constant. All of the sensor embodiments 90 account for saw blade 38 wear by dynamic determination of position of first contact which is not based on a predefined size of the saw blade 38. Instead, the sensors 90 determine when contact is being made, and adjust the position of the blade 38 or the elongate object 8 accordingly.

Also, as will be appreciated using stepper motors with fine control and a microcontroller for actuation and control of the movement of the blade with respect to the base implies that equally precise location sensing is possible by simply tracking the number of steps of the stepper motors from a reference point. Given the additional accuracy possible by gear reduction from the stepper motors to linear actuators position can be accurately inferred at the same time motion is induced.

The above description of the operation of the guidewire or catheter element or other elongate object cutting system 6 describes the different roles served by the clamp 52. When the circular saw blade 38 is making a cut in the guidewire or catheter element or other elongate object 8, the clamp 52 holds the guidewire or catheter element or other elongate object 8 steady. When the cut has been made in the guidewire or catheter element or other elongate object 8, the guidewire or catheter element or other elongate object 8 is fed through the clamp 52 by causing the clamp to disengage from around the guidewire or catheter element or other elongate object 8. After being disengaged, the guidewire or catheter element or other elongate object 8 is fed through the clamp 52 until the next incision point on the guidewire or catheter element or other elongate object 8 is in position relative to the saw blade 38. The clamp 52 re-engages so as to be disposed snugly around the guidewire or catheter element or other elongate object 8 to again prevent movement of the guidewire or catheter element or other elongate object 8 during cutting.

It should be recognized from the description above that the width of a cut into the guidewire or catheter element or other elongate object 8 is limited to the width of the circular saw blade 38. A wider cut therefore requires that the guidewire or catheter element or other elongate object 8 be advanced slightly past the saw blade 38. However, advancement does not take place while making a cut. The saw blade 38 must be withdrawn so that the clamp 52 can disengage from around the guidewire or catheter element or other elongate object 8 while it is advanced. This is necessary because allowing cutting of the guidewire or catheter element or other elongate object 8 when the clamp is disengaged would create an imprecise or useless cut.

Figure 9A:
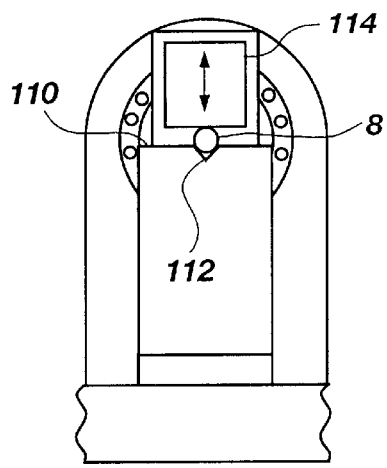
FIG. 9A is a front view of a clamp in another embodiment of the system.
Figure 9B:
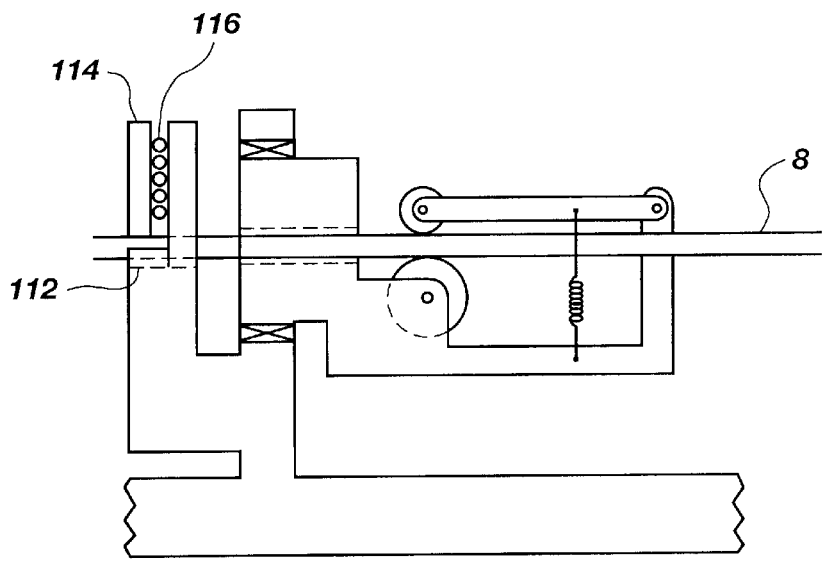
FIG. 9B is a side view of the clamp of FIG. 9A.

Variations of the preferred embodiment are illustrated in FIGS. 9A end 9B which show that the clamping means 52 has been modified. As can be seen in FIG. 9A, a stationary support surface 110 is provided with a slot 112 therein for supporting the guidewire or catheter element or other elongate object 8 from below. The slot 112 guides and holds the guidewire or catheter element or other elongate object 8 before, during and after cutting. Holding the guidewire or catheter element or other elongate object 8 not only allows more precise cutting, but prevents damage to the guidewire or catheter element or other elongate object 8 which might otherwise occur. A movable clamping member 114 or anvil is also provided to thereby apply force to the guidewire or catheter element or other elongate object 8 which is clamped between the anvil 114 and the slotted support surface 110. FIG. 9B also shows that the anvil 114 has a mechanism 116 which allows the anvil 114 to move vertically with respect to the support surface 110. In FIG. 9B the vertical movement mechanism 116 is shown as bearings.

Figure 9C:
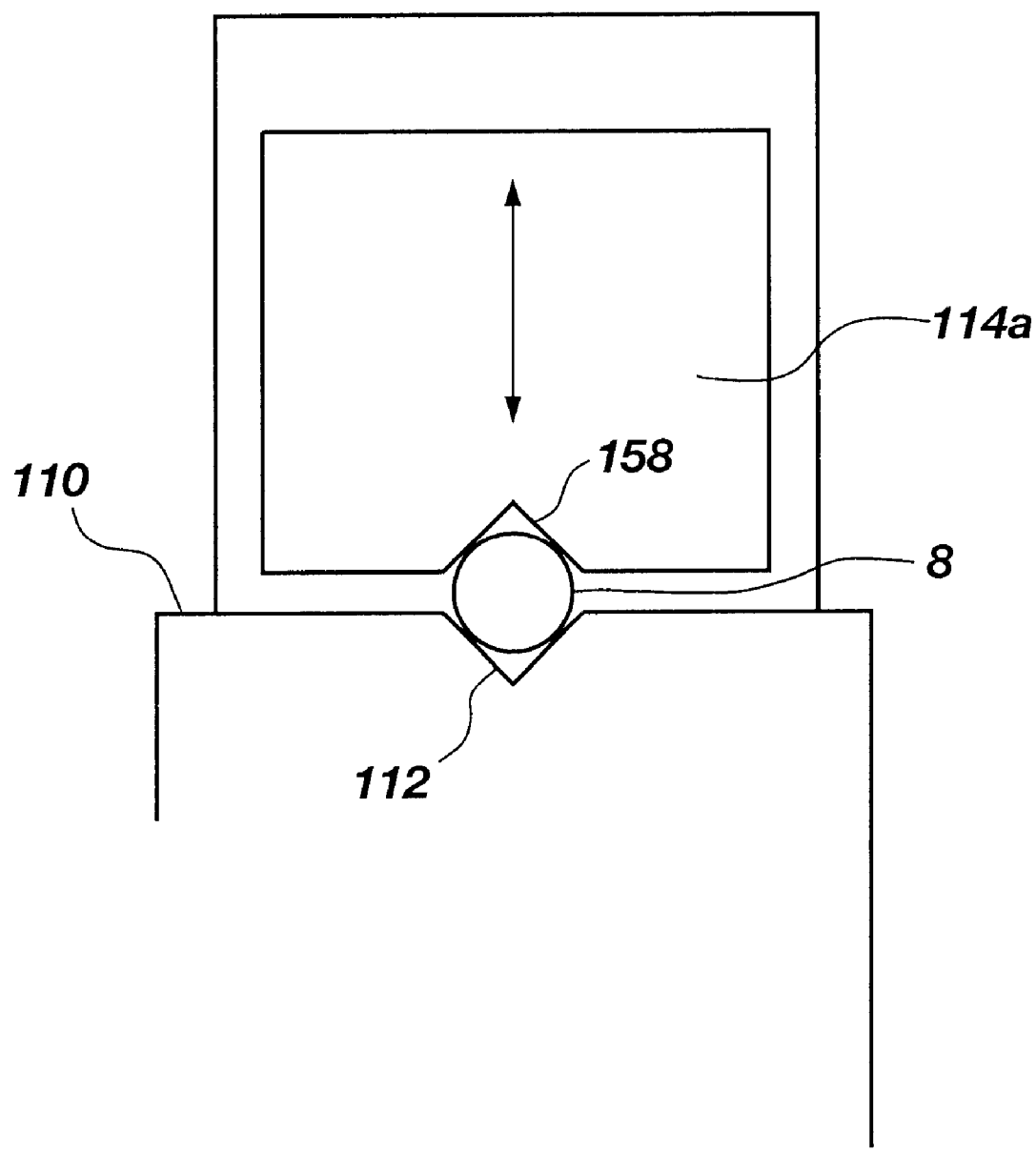
FIG. 9C is a front elevational view of another embodiment of the clamp.

FIG. 9C is provided to illustrate an alternative embodiment of the anvil 114a. As shown, the anvil 114a has a slot 158 which will hold the guidewire or catheter element or other elongate to object 8 more securely for cutting.

FIG. 10 illustrates a modification to the spindle 32 and saw blade 38 arrangement shown in FIGS. 1A and 1B. Specifically, a plurality of saw blades 38 are shown as being mounted in parallel on the same spindle 32. This also means that the saw blades 38 are necessarily coaxial. It is also preferred that the saw blades 38 have the same diameter so that no individual saw blade 38 makes a deeper incision in the guidewire or catheter element or other elongate object 8 than any of the others. However, it should be apparent that if the spindle 32 or the saw blades 38 are easily detachable from the system 6, then saw blades of varying diameters might be mounted on the same spindle 32 to achieve a consistent pattern of cuts having different depths.

FIG. 11A shows a clamp mechanism 120 which should be used in conjunction with the multiple saw blade 38 assembly of FIG. 10. The clamp mechanism 120 is capable of holding a catheter 8 in place while the catheter 8 is cut by the plurality of saw blades 38. This is accomplished by providing a clamping surface 122 having a depression or slot 124 for receiving the catheter 8. Coupled to the clamping surface is a leaf spring 126. The leaf spring 126 is comprised of several fingers 128 which force the catheter 8 to remain in the slot 124 while it is cut. Disposed perpendicular to the slot 124 and extending from the clamping surface 122 completely through the clamping mechanism 120 to a back side 136 are a plurality of slots 130 (which make clamp fingers 132) through which the saw blades 38 are extended to thereby cut the catheter 8. The forgers 128 of the leaf spring 126 are typically spaced apart a distance which is equal to the spacing between the plurality of slots 130. This ensures that the saw blades 38 do not inadvertently make contact with the leaf spring fingers 128 while cutting the catheter 8.

To allow the catheter 8 to he fed through the slot 124 in the clamping surface 122, there must be a mechanism for raising the fingers 128 of the leaf spring 126 from off the clamping surface 122. FIG. 11A shows a plurality of holes 134 through the clamping mechanism 120, one hole 134 per clamp finger 132. FIG. 11B shows these holes 134, and more importantly, the plurality of push rods 136 which extend through the holes 134 from the back side 136 of the clamp mechanism 120 to the clamping surface 122. Mechanism 237 simultaneously pushes the plurality of push rods 136 when the clap mechanism 120 is instructed to disengage the clamp and move the catheter 8.

Figure 12:
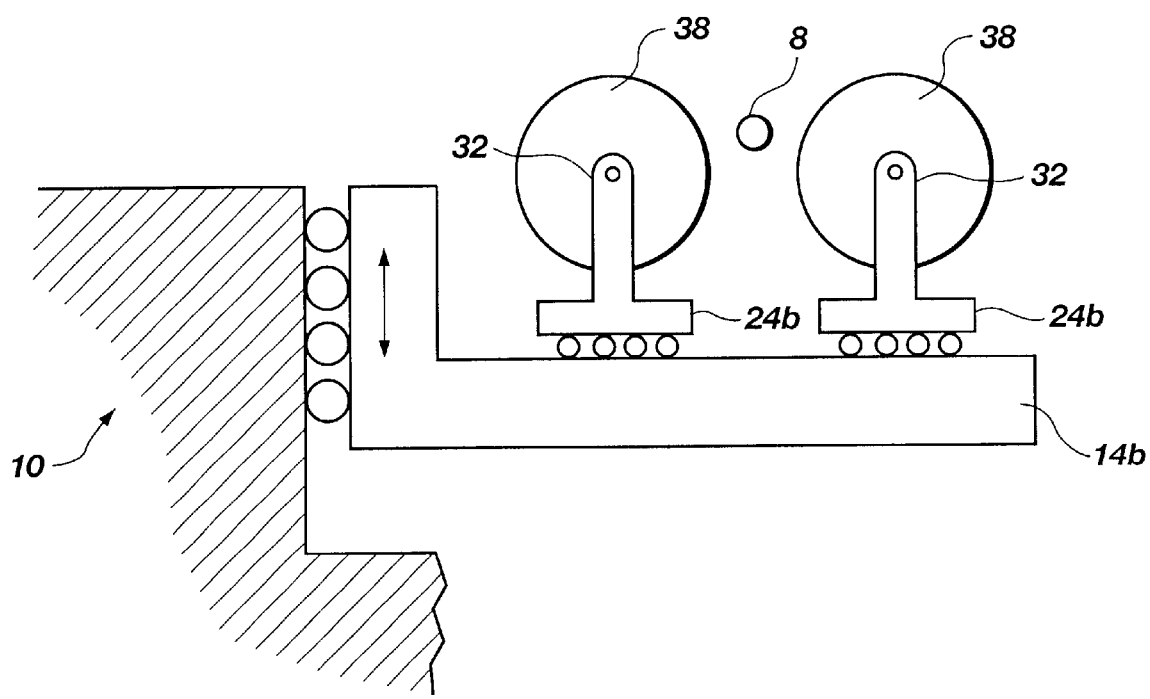
FIG. 12 is a front view of a portion of the system in another embodiment.

FIG. 12 is an illustration of another alternative embodiment of the present invention. The vertically movable member 14b is shown having another shape which enables it to have disposed thereon two horizontal movable members 24b, each having its own associated saw blade or blades 38. This embodiment enables the catheter 8 to be simultaneously cut at different circumferential defined points on the catheter surface. This is especially useful in making cuts in catheters which having multiple incisions, for example, on diametrically opposed positions on the catheter 8.

It should be noted that while the preferred embodiment has been defined as having a horizontally movable member with the spindle for the saw blade coupled thereto, the placement of the vertically and horizontally movable members can be switched as shown in FIG. 13. In this arrangement, the horizontally movable member 144 is coupled to the base member 142 and the vertically movable member 146, and the vertically movable member 146 has a spindle 148 rotatably coupled thereto.

In another alternative embodiment of the present invention, shown in FIG. 14, a lever arm 150 is pivotally connected to the base member 154, and is capable of movement in at least two degrees of freedom so that it can move vertically and horizontally to position a spindle end 152.

Another aspect of the invention which should be clarified is that rotating the catheter is not limited to using a rotatable clamping mechanism. For example, the clamp can be non-rotatable and disengaged to enable the catheter feeding mechanism to rotate the catheter, and then re-engage the clamp to make additional incisions. Furthermore, the clamp and the catheter feeding mechanism can be rotated together before additional incisions are made.

Alternative aspects of the invention include the substitution of a non-mechanical cutting instrument for the rotating blade of the presently preferred embodiment. For example, a laser can be provided for cutting through materials which are mounted on the system.

It should also be realized that rotating blades are not the only type of mechanical blade which can be utilized. Conventional "sawing" blades can also be provided.

FIG. 15 is a schematic view of an alternative embodiment of the invention. This embodiment is similar in most respects to that of FIG. 1 and includes most of same elements. For a complete description of the common elements, see the description of FIG. 1 above. However, rather than having a vertically movable member 14 as in FIG. 1, this embodiment comprises only a horizontally movable member 224 which is slidingly coupled to base member 210 at horizontal coupling face 18. In this embodiment the horizontally movable member is vertically positioned so that the center of blade 38 is in substantial alignment with the center of the catheter 8.

Horizontally movable member 224 is connected to and actuated by a linear motion transducer 200, which is affixed to base 210. Linear motion transducer 200 may comprise any device suitable for causing very accurate, controllable forward and backward horizontal motion of member 224, such as electric motors, hydraulic systems, etc. In the preferred embodiment, the linear motion transducer 200 comprises an electric stepping motor, which is coupled to member 224 via a highly accurate gear reduction system (not shown) similar to that found in a micrometer. This configuration advantageously allows motion of the horizontally movable member in very small increments.

Also affixed to base 210 is a sensor 202, which is connected via linkage 204 to horizontally movable member 224. Sensor 202 provides independent detection and measuring of the forward or backward position of horizontally movable member 224, and is connected to controller 80 as described in more detail below. Sensor 202 is preferably an optical linear encoder, but may alternatively comprise a rotary optical encoder, a linearly variable differential transformer (LVDT), a linearly variable differential capacitor (LVDC), or any other suitably accurate means of measuring the physical position of member 224. Optical encoder, LVDT's, LVDC's, and similar devices are commercially available and well known to persons skilled in the art.

Sensor 202 is optional, however. As an alternative, the extension and retraction of member 224 may simply be monitored through control of transducer 200, by monitoring the amount of extension of the stepper motor. For example, a rotary optical encoder may be interconnected to the gear reduction system that is part of transducer 200, and gauge the amount of linear extension of member 224 by monitoring the total angular rotation of the optical encoder at any given time. Rotation of the rear reduction system may be controlled by software in the controller which receives feedback from the optical encoder.

Figure 16:
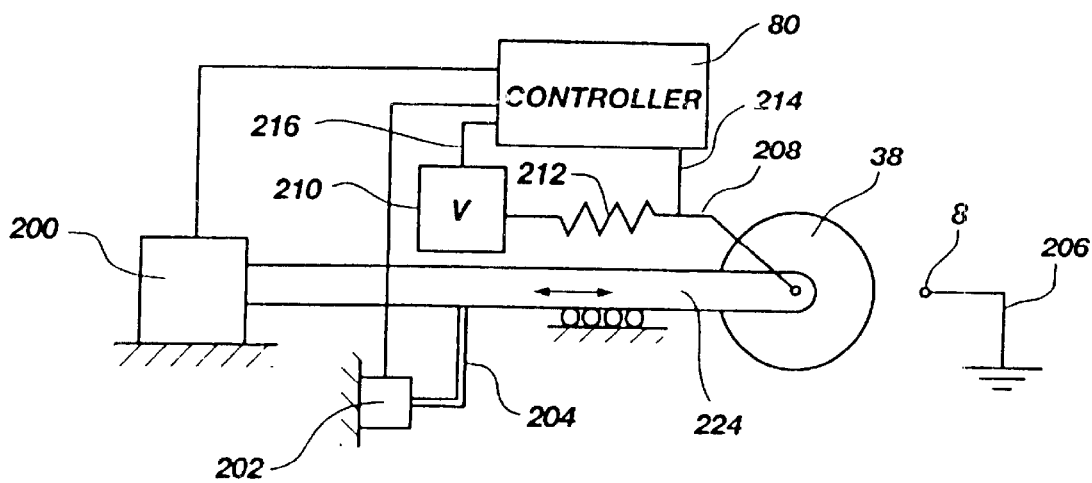
FIG. 16 is a schematic illustration of the system show in FIG. 15.

When making precision cuts in a catheter or guidewire, it is desirable to correct for wear of the cutting blade, and also to have a means for precisely measuring and controlling the depth of cut. FIG. 16 provides a partial schematic view of the embodiment of FIG. 15 which incorporates an electrical contact detection system to provide these desirable features. In this system, the catheter 8, which is electrically conductive, is grounded via line 206. Blade 38, which is also electrically conductive, is connected via line 208 to voltage source 210 through resistor 212, thus creating a voltage potential between blade 38 and catheter 8. It will be apparent that any cutting fluid of coolant used in conjunction with this system will need to be non-conductive.

When blade 38 is a separated from catheter 8, the voltage in line 208 will he the same as the voltage produced by the voltage source 210, as reduced by resistor 212. However, when blade 38 approaches to within a few millionths of an inch of the surface of catheter 8, which is grounded, electric current will arc across the gap, causing an immediate voltage jump in line 208, The direction of this voltage jump will be dependent upon whether the system operates on direct current of alternating current. By detecting the instant that the voltage jumps and comparing this with known information regarding the position of horizontal member 224, the system can continuously verify and adjust its operation to produce highly accurate and consistent cuts.

Line 214 connects line 208 to controller 80, which is thus able to gauge the voltage in line 205, and detect when that voltage drops to zero. Controller 80 is connected back to voltage source 210 through line 216, and also connected to linear motion transducer 200 and sensor 202 for feedback and control. The controller is thus able to very accurately monitor and adjust the depth of cut by detecting the moment of contact between the blade 38 and catheter 8, sensing, through sensor 202, the exact position of member 224 when such contact is made, and adjusting the motion of member 22 through signals to transducer 200.

As an operative example, as blade 38 becomes worn through use, its diameter will decrease, causing it to contact the surface of the catheter 8 at a later and later point in its horizontal motion. If the depth of cut were determined solely by transducer settings established at the beginning of an operation, the cuts would thus become gradually shallower, thus affecting the quality and characteristics of the finished product. However, because the controller 80 senses the contact of the blade 38 with the catheter 8 at the beginning of each cut, and simultaneously receives true position information from sensor 202, the controller can signal transducer 200 to extend member 224 the appropriate distance each time to maintain the proper depth of cut.

Figure 17:
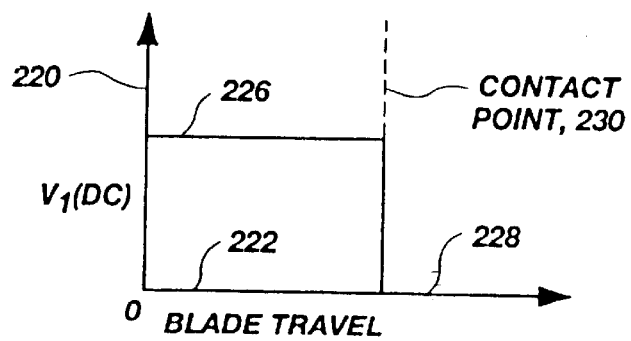
FIG. 17 is a graph of the line voltage vs. blade travel as shown in FIG. 16.

It will be apparent that the system depicted in FIG. 16 could be constructed to operate on either direct current (DC) or alternating current (AC). FIG. 17 is a graph of the line voltage $V_1$ (vertical axis 220) versus blade travel (horizontal axis 222) toward the cylindrical object, for a DC contact detection circuit. The voltage $V_1$ is constant as shown at 226 when the blade and catheter are separated, but jumps to zero as shown at 218 when the blade reaches the contact point 230, a few millionths of an inch from the surface of the catheter. In a preferred embodiment the DC line voltage $V_1$ is 5 volts, to make the system compatible with standard digital controllers. The voltage state is thus recognizable by the controller as a digital signal representing on or off, contacting or not contacting.

Figure 18:
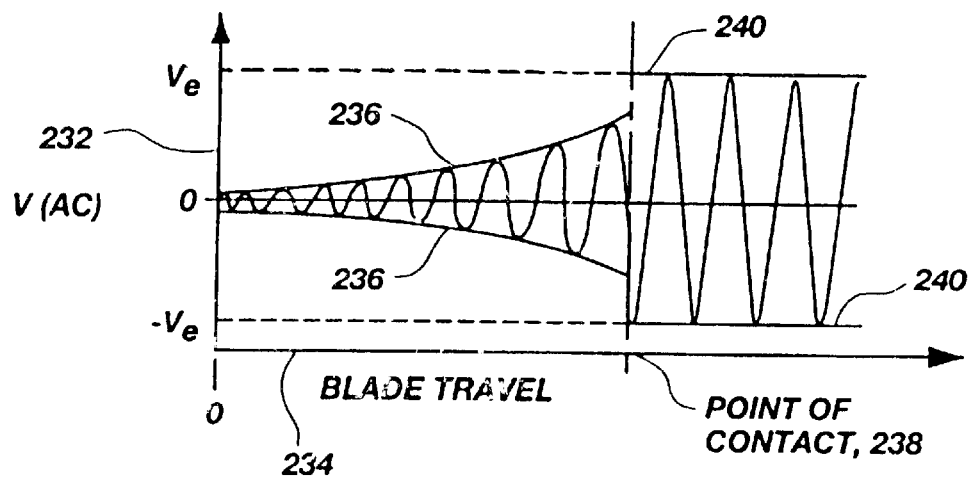
FIG. 18 is a graph of the induced voltage vs. proximity to the surface of the cylindrical object in an AC embodiment of the system shown in FIG. 16.

When using AC, the system of FIG. 16 not only detects contact between the blade and the catheter, but also detects proximity using capacitative characteristics. With AC, the voltage potential between the blade and the catheter will have both a positive excitation voltage ($V_e$) and a negative excitation voltage ($=V_e$). FIG. 18 provides a graph of the excitation voltage $V_e$ (vertical axis 232) versus proximity to the surface of the cylindrical object (horizontal axis 234) for an AC contact detection circuit. As the blade approaches the surface of the catheter, the excitation voltage $V_e$ will increase in a predictable manner, from zero to some voltage between $V_e$ and $-V_e$, the variation of this voltage being represented by curves 236. Those skilled in the art will recognize that curve 236 can be predicted using principles of capacitance, and thus a controller receiving a signal representative thereof can calculate the distance between the blade and the catheter based upon the detected $V_e$.

When the blade reaches the contact point 238, a few millionths of an inch from the surface of the catheter, rather than jumping to zero, the detected voltage will immediately jump to the full value of $V_e$ as shown at 240. As with the DC embodiment, by detecting this jump in AC voltage, the controller can accurately detect the location of the edge of the catheter relative to the blade and member 224, and adjust the system as necessary.

Figure 19:
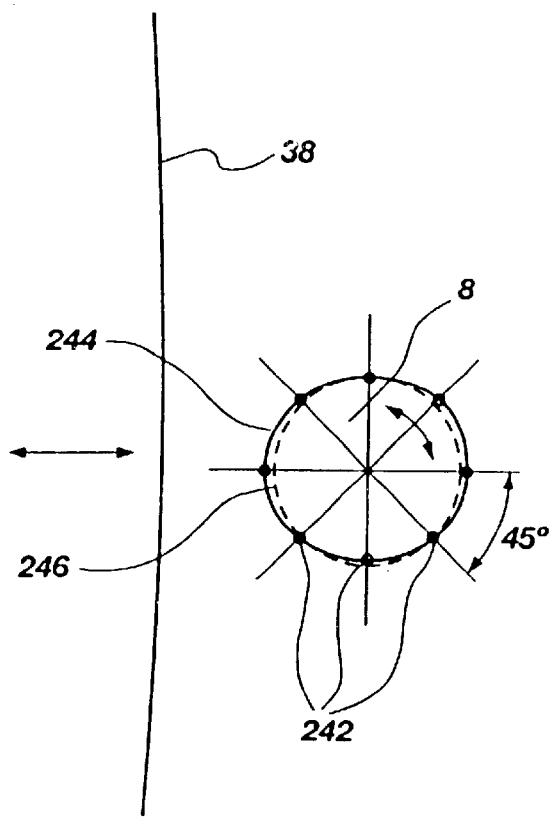
FIG. 19 is a front detailed cross-sectional view illustrating a system for detecting defects in the shape of a cylindrical object.

An additional advantage of this system is the ability to correct for irregularities in the material of the catheter. It will be apparent that the very fine solid or tubular wires anticipated by this invention may suffer from manufacturing flaws which are typical to wires of all kinds, such as variations in diameter, out-of-roundness, etc. Moreover, these irregularities may vary along the length of the wire. Detection and correction for these flaws is possible with the present system. FIG. 19 shows a cross-sectional view of the system for detecting defects in the shape of the cylindrical object.

When the system of FIG. 16 is in operation, the location of the surface of the catheter 8 is detected each time the blade 38 contacts it. As cuts are made in the catheter at various angular locations 242, shown here as every 45 degrees, the roundness and dimension of the catheter cross-section can be detected and recorded. As shown in FIG. 19, the outer surface 244 of the catheter is irregular with respect to a theoretical round cross-section 246.

Because the system detects this irregularity, controller 80 can compensate for it by adjusting the depth of any given cut to produce a catheter with the desired properties. For example, if the catheter is detected to be 5% out of round (either large or smaller than the theoretical diameter) about a first axis, and 10% out of round (larger or smaller) about a second axis, the system may compensate by adjusting the depth of cuts relative to the first axis by 5% (either shallower or deeper), and relative to the second axis by 10% (shallower or deeper). Alternatively, the controller may be programmed to calculate the moment of inertia of the detected cross-sectional shape relative to various axes, and adjust the depth of any given cut to ensure that the resulting catheter has the desired moment of inertia at the given location, despite an irregular shape. As cutting proceeds, the irregularities may vary, but this will also be detected in an ongoing manner as described.

Additional advantages may also be realized with the present invention. For example, a series of cuts made as described may be formed on a catheter or guidewire to create an SPC symbol or bar code for identification. The inventors have found that a series of cuts can easily accommodate 100 bits of information, which may be used to indicate the batch number of a particular catheter, its material suppliers, its date of manufacture, etc. Such a bar code could be located at any location along the catheter, and could be used, for example, to allow patient specific manufacture of a catheter guidewire. If a patient required a particular sensitive catheter procedure and presented uniquely difficult vascular anatomy, but could wait for the procedure for a few days, a physician could send MRI or other diagnostic information indicating that anatomy to the manufacturer of the catheter. Then, a catheter or having the location specific flexibility particularly designed for that patient could be custom produced, and micromachined with a unique SPC code. When the physician receives that catheter, he simply scans the code to verify that he has the correct item, end then begins the medical procedure.

It is to be understood that the above-described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A micro-machining system configured for cutting an elongate element of small transverse dimension having a lengthwise axis, comprising:
   a controller programable to enable control of cuts in the elongate element with respect to each other in terms of position along and around the lengthwise axis and to a depth desired;
   a clamp configured to enable repeatedly releasing and then holding the elongate element in a fixed position for cutting the elongate element transversely relative to the lengthwise axis;
   a pinch roller feed configured to advance the elongate element and to rotate the elongate element about the lengthwise axis of the elongate element, thereby moving the elongate element so that the elongate element is disposed in a position for cutting;
   a contact reference position sensor; and
   a cutter configured for forming at least one precision cut in the elongate element to the depth desired into the elongate element from a sensed first contact by the cutter with the elongate element.

2. A micro-machining system as in claim 1, wherein the contact reference position sensor comprises an electric circuit completed by contact between the cutter and the elongate element.

3. A micro-machining system as in claim 2, wherein the circuit is an AC circuit and proximity of the cutter to the elongate element is sensed before contact is made.

4. A micro-machining system as in claim 1, wherein the contact reference position sensor comprises an optical sensor which senses contact between the cutter and the elongate element.

5. A micro-machining system as in claim 1, wherein the cutter is a rotating cutting blade forming a kerf of a width less than 0.003 inches.

6. A micro-machining system as in claim 1, where in movements of the pinch roller and the cutter are facilitated by stepper motors controlled by the controller.

7. A micro-machining system as in claim 1, further comprising another position sensor configured to provide a feedback to the controller of position change of the cutter moved under control of the controller.

8. A micro-machining system as in claim 1, wherein the contact position sensor is configured to sense of least one of a) an amount of blade wear on the cutter comprising a cutting blade; b) an asymmetry of the elongate element about the lengthwise axis at a given point along tire length thereof.

9. A system for micro-machining an elongate element having a lengthwise axis, comprising:
   a controller configured to control operation of the system, programable to produce micro-machined elongate elements of desired configurations;
   a clamp configured to engage and release the elongate element under control of the controller;
   manipulating means configured to move the elongate element along the lengthwise axis and to rotate the elongate element about the lengthwise axis under the control of the controller, further comprising an actuator controlled by the controller configured to rotate the elongate element, and an actuator controlled by the controller configured to move the elongate element along the lengthwise axis;
   a saw blade configured to form cuts of small dimensions in the elongate element and an actuator configured to move the saw blade toward and away from the elongate element under control of the controller;
   a contact reference point identification system configured to provide a signal interperatable by the controller indicating that the saw blade has approached the elongate element and just made contact therewith without appreciable depth of cut to thereby control depth of cut from a contact reference point into the elongate element by the saw blade,
   whereby the elongate element is clamped to hold the elongate element in a fixed position, and a first cut of precisely controlled depth is made, and the elongate element is released and at least one of rotated and moved along and about the lengthwise axis so that a second precise cut is made at a desired depth in a desired position relationship to the first cut.

10. A system as in claim 9, further comprising a stepper motor under control of the controller configured to actuate at least one of the manipulating means and the saw blade.

11. A system as in claim 9, wherein said actuator facilitating movement of the saw blade toward and away from the elongate element further comprises a caliper and a stepper motor operatively connected to the caliper, configured to position the saw blade with respect to the elongate element with precision, whereby a depth of cut with respect to the contact reference point is precisely controlled.

12. A system as in claim 11, wherein the contact reference point identification system further comprising a movement sensor configured to sense movement of the saw blade toward and away from the elongate element wherein feedback control of the saw blade position is facilitated.

13. A system as in claim 12, wherein the movement sensor 19 at least one of a linear differential transformer and a linearly variable differential capacitor.

14. A system as in claim 9, wherein the actuator configured to move the elongate element along the lengthwise axis further comprising a stepper motor under control of the controller operatively coupled to the manipulating means to advance the elongate element.

15. A system as in claim 9, wherein the actuator configured to rotate the elongate element further comprising a stepper motor under control of the controller operatively coupled to the manipulating means to rotate the elongate element.

16. A system as in claim 9, wherein the contact reference point identification system comprises an electrical circuit completed by contact of the; saw blade and the elongate element.

17. A system as in claim 16, wherein the circuit is a DC circuit.

18. A system as in claim 17, wherein the circuit is an AC circuit.

19. A system as in claim 18, wherein proximity of the saw blade to the elongate element is sensed by induced current from the AC circuit.

20. A system as in claim 16, wherein the contact reference point identification system is configured to quantify one of an asymmetry and an out-of-round condition of the elongate element.

21. A system as in claim 9, wherein the saw blade forms a kerf of less than 0.003 inches.

22. A system as in claim 9, wherein said actuators of the manipulating means comprise calipers turned by stepper motors.

23. A system for forming cuts in a small-diameter elongate element having a lengthwise axis, comprising:
   a controller configured to control operation of the system, programable to produce micro-machined elongate elements of desired configurations in diameter sizes usable as catheters and guidewires for invasive medical procedure in a human body;
   a clamp configured to engage and release the elongate element under control of the controller;
   manipulating means including a pinch roller assembly configured to grasp the elongate element, and move the elongate element along the lengthwise axis and to rotate the elongate element about the lengthwise axis under the control of the controller, further comprising an actuator comprising a stepper motor controlled by the controller configured to rotate the elongate element, and an actuator comprising a stepper motor control led by the controller configured to move the elongate element along the lengthwise axis;
   a saw blade configured to form cuts of small dimensions in the elongate element and to be movable toward and away from the elongate element by an actuator comprising a stepper motor turning a caliper under control of the controller;
   a contact reference point identification system comprising an electrical circuit configured to provide a signal interperatable by the controller indicating that the saw blade has approached the elongate element and just made contact therewith without appreciable depth of cut to thereby control depth of cut from a contact reference point into the elongate element by the saw blade,
   whereby the elongate element can be clamped to hold the elongate element in a fixed position, and a first cut made, then the elongate element is released and moved by being at least one of rotated and moved along and about the lengthwise axis so that second precise cut is made to a desired depth at a desired position in relationship to the first cut.

* * * * *